(12) United States Patent
Wang et al.

(10) Patent No.: US 7,935,527 B2
(45) Date of Patent: May 3, 2011

(54) METHODS FOR CULTURING HUMAN EMBRYONIC STEM CELLS

(75) Inventors: Mei-Chih Wang, Toufen Township, Miaoli County (TW); Mei-Hwei Fan-Chiang, Madou Township, Tainan County (TW); Hui-Ti Lin, Sindian (TW); Chin-Yu Lin, Jhongpu Township, Chiayi County (TW)

(73) Assignee: Industrial Technology Research Institute (TW)

( * ) Notice: Subject to any disclaimer, the term of this patent is extended or adjusted under 35 U.S.C. 154(b) by 894 days.

(21) Appl. No.: 11/008,929

(22) Filed: Dec. 13, 2004

(65) Prior Publication Data

US 2005/0158852 A1  Jul. 21, 2005

(30) Foreign Application Priority Data

Dec. 31, 2003  (TW) ................ 92137762 A

(51) Int. Cl.
*C12N 5/00* (2006.01)
(52) U.S. Cl. ...................................... 435/325
(58) Field of Classification Search ............... None
See application file for complete search history.

(56) References Cited

U.S. PATENT DOCUMENTS

2003/0073234 A1  4/2003  Amit et al.

FOREIGN PATENT DOCUMENTS

WO   WO 2004/055155    *   7/2004
WO   WO 2004/055155 A2    7/2004

OTHER PUBLICATIONS

Amit et al., Developmental biology, 2000, 227: 271-278.*
Richards et al., Nature Biotechnology, 2002, 20: 933-936.*
Amit et al., Dev Biol, 2000, 227: 271-278.*
Michel Amit et. al.; *Clonally Derived Human Embryonic Stem Cell Lines Maintain Pluripotency and Proliferative Potential for Prolonged Periods of Culture*; 2000; Developmental Biology 227; pp. 271-278.

* cited by examiner

*Primary Examiner* — Ileana Popa
(74) *Attorney, Agent, or Firm* — Bacon & Thomas, PLLC

(57) ABSTRACT

The present invention discloses a method for improving growth and survival of single human embryonic stem cells. The method includes the step of obtaining a single undifferentiated HES cell; mixing the single undifferentiated cell with an extracellular matrix (ECM) to encompass the cell; and inoculating the mixture onto feeder cells with a nutrient medium in a growth environment. Therefore the single cells can survive, proliferate and grow in vitro.

13 Claims, 4 Drawing Sheets

(a)

(b)

(c)

(d)

(a)           (b)

(c)           (d)

(a)

(b)

(a)

(b)

METHODS FOR CULTURING HUMAN EMBRYONIC STEM CELLS

BACKGROUND OF THE INVENTION

1. Field of the Invention

The invention relates to methods for culturing human embryonic stem (HES) cells. More particularly, to methods for culturing single HES cells in a substantially undifferentiated state.

2. Description of Related Art

Human embryonic stem (HES) cells are pluripotent cell lines that have been derived from the inner cell mass (ICM) of blastocyst stage embryos. HES cells have the potential to develop into any type of cells and to generate any types of tissues, organs or body parts, including a whole organism. As such, it is expected that the ability to provide normal clonal HES cells on demand and to manipulate the differentiation thereof will provide a powerful tool capable of driving radical advances in the biomedical, industrial and scientific fields.

Potential applications of HES cells are far ranging and include drug discovery and testing, generation of cells, tissues and organs for use in transplantation, production of biomolecules, testing the toxicity and/or teratogenicity of compounds and facilitating the study of developmental and other biological processes. For example, diseases presently expected to be treatable by therapeutic transplantation of HES cells or HES-derived cells include Parkinson's disease, cardiac infarcts, juvenile-onset diabetes mellitus, and leukemia (Gearhart J. Science 282: 1061-1062, 1998; Rossant and Nagy, Nature Biotech. 17: 23-24, 1999).

There are, however, significant hurdles to the practical exploitation of HES cells.

To maintain HES cells in an undifferentiated state, HES cells are usually cultured on feeder cells. The feeder cells can secrete factors needed for stem cell self-renewal and proliferation, while at the same time, inhibit their differentiation.

Commonly used feeder cells includes a primary mouse embryonic fibroblast (PMEF), a mouse embryonic fibroblast (MEF), a murine fetal fibroblast (MFF), a human embryonic fibroblast (HEF), a human fetal muscle cell (HFM), a human fetal skin cell (HFS), a human adult skin cell, a human foreskin fibroblast (HFF), a human adult fallopian tubal epithelial cell (HAFT) and a human marrow stromal cells (hMSCs) (International Patent Publication Nos. WO 03/02944 and 03/014313; J. H. Park et al., Biol Reprod. 69:2007-2017, 2003; M. Amit et al., Biol Reprod. 68 (6):2150-2156, 2003; Outi Hovattal et al., Hum. Reprod. 18 (7): 1404-1409, 2003; Richards, M. et. al, Nat Biotechnol. 20(9):933-936, 2002; James A. et al., Science 282 (6):1145-1147, 1998; Linzhao Cheng et al., Stem Cells 21:131-142, 2003).

The HES cells can also be cultured on an extracellular matrix (ECM) instead of feeder cells.

Commonly used matrix includes the basement membrane preparation extracted from Engelbreth-Holm-Swarm (EHS) mouse sarcoma (e.g. Matrigel™), or bovine-fibronectin/laminin. These matrix are usually supplemented with a mouse embryonic fibroblast (MEF) conditioned medium, or a synthetic medium supplemented with bovine serum and growth factors (Xu et al. Nat. Biotechnol. 19 (10):971-974, 2001; International Patent Publication No. WO 03/020920; U.S. patent Pub. No. 20030017589).

Once established and expanded, HES cells are routinely passaged by manual dissociation. Unlike mouse embryonic stem cells, the HES cells cannot be enzymatically dispersed into single cells without causing undesirable death or differentiation. When the sizes of colonies reach 1-to-2 mm diameter, they are cut into several pieces with a pulled glass pipette and the colony pieces are inoculated onto new feeder cells or extracellular matrix (ECM) for sub-culturing. Colony piece sizes of about 50 to 100 cells were optimal.

However, such culture method for HES cells described above introduces disadvantages in the scaling up and downstream manipulation and experimentation of HES cells. Some of these disadvantages are (1) the labor intensiveness in having to passage by manual dissociation, unlike other cells that can be passaged by exposure to enzymes; (2) the constraints of scaling up large numbers of HES cells because the propagation of undifferentiated HES cells can not be achieved by utilizing single cells; (3) a small cluster of HES cells makes the transfection procedure more difficult than that of single cells and therefore complicates both experimental procedures and results.

To establish culture conditions that allow the growth and survival of single undifferentiated HES cells is therefore an urgent necessity to help overcome these disadvantages and lead the prospects of large/bulk scale HES cell production.

An article by Amit et al. (Dev. Biol. 227: 271-278,2000; U.S. patent Pub. No. 20030073234) is entitled Clonally Derived Human Embryonic Stem Cell Lines Maintain pluripotency and Proliferative Potential for Prolonged Periods of Culture Although this publication reported that HES cell line H9 could be subcloned as single cells on feeder cells, our data indicate that HES-3 lines could not be propagated by using such method.

There is need, therefore, to provide an alternative method for culturing single HES cells.

SUMMARY OF THE INVENTION

The present invention provides a method for culturing undifferentiated human embryonic stem (HES) cells. The method described herein provides improved culturing conditions that allow the growth and survival of single undifferentiated HES cells. The method is useful for establishing a clonal HES cell line. Additionally, the method has important applications in gene transfection and expression.

Accordingly, the present invention provides a method of culturing single undifferentiated HES cells. The method comprises the steps of obtaining a single undifferentiated HES cell; mixing the single undifferentiated cell with an extracellular matrix (ECM) to encompass the cell; and inoculating the mixture onto feeder cells with a nutrient medium in a growth environment.

In the present invention, the extracellular matrix can be Matrigel or human extracellular matrix. The extracellular matrix can also be prepared from an isolated matrix component or a combination of components selected from the group consisting of collagen, elastin, fibronectin, laminin and fibrillin. The feeder cells can be selected from the group consisting of, but not limited, primary mouse embryonic fibroblasts (PMEF), mouse embryonic fibroblasts (MEF), murine fetal fibroblasts (MFF), human embryonic fibroblasts (HEF), human fetal muscle cells (HFM), human fetal skin cells (HFS), human adult skin cells, human foreskin fibroblasts (HFF), human adult fallopian tubal epithelial cells (HAFT) and human marrow stromal cells (hMSCs).

Once surviving, the single cell can proliferate. Further, a clonal embryonic stem cell line is established.

The present invention successfully addresses the shortcomings of the presently known configurations by providing methods of culturing single undifferentiated HES cells using an ECM and feeder cells. Single cells can retain a high survival rate and an undifferentiated proliferation capacity in such culture conditions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a: control; FIG. 1b: an extracellular matrix made from HES cells; FIG. 1c: Matrigel™; and FIG. 1d: collagen III.

FIG. 2a: control; FIG. 2b: an extracellular matrix obtained from HES cells; FIG. 2c: Matrigel™; FIG. 2d: collagen III.

FIG. 3a: fluorescence image of one colony derived from transfected single undifferentiated HES-3 cells; FIG. 3b: bright-field image of the same colony shown in FIG. 3a.

FIG. 4a: fluorescence image of one transfected cell colony; FIG. 4b: computer-generated overlay of a bright-field and fluorescence image of the same colony shown in FIG. 4a.

DETAILED DESCRIPTION OF THE PREFERRED EMBODIMENT

Figure 1:
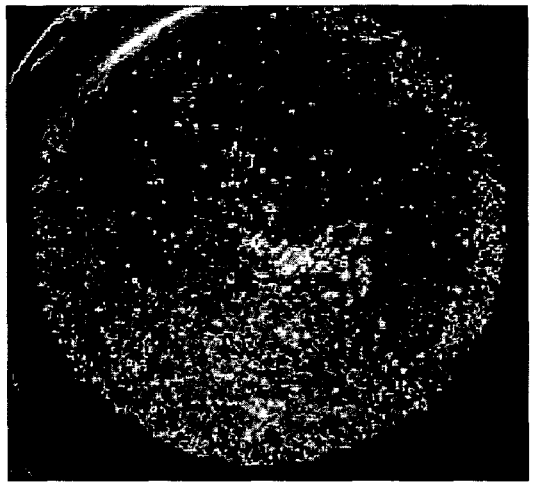
FIGS. 1a-d illustrate the expression of alkaline phosphatase of 6-day-old colonies derived from single undifferentiated HES-3 cells encompassed with various extracellular matrix (ECM) on mitomycin-C treated human foreskin fibroblast (HFF) feeder cells in the HES medium.
Figure 1:
Figure 1:
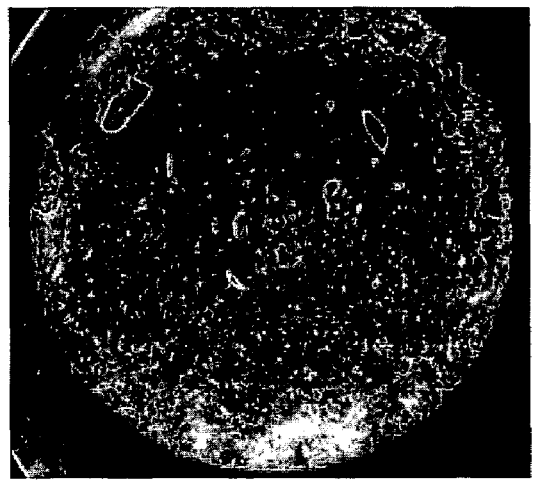
Figure 1:
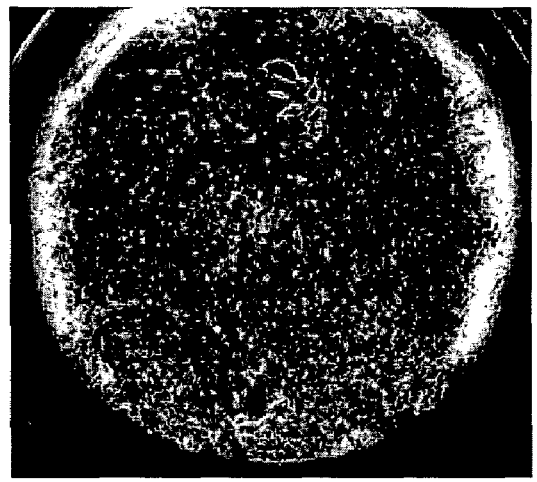

The present invention provides a method for culturing undifferentiated human embryonic stem cells. The method is useful for establishing a clonal HES cell line. Additionally, the method is suitable for gene transfection and expression studies.

The principles and operation of the methods of improving the growth and survival of single undifferentiated HES cells according to the present invention may be better understood with reference to the drawings and accompanying descriptions.

Before explaining at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

To maintain HES cells in an undifferentiated state, the HES cells have to be in the conditions that maintain cell proliferation, inhibit ES cell differentiation and preserve pluripotency. Such culturing conditions are typically achieved by utilizing feeder cells that secrete factors needed for stem cell proliferation, while inhibit their differentiation. The culturing conditions can also be achieved by an extracellular matrix (ECM) instead of feeder cells. However, these culturing conditions are suitable for culturing small clusters rather than for single cells.

Thus, according to the present invention, a method to improve the culture conditions that allow the growth and survival of single undifferentiated HES cells is provided.

The method of culturing single undifferentiated HES cells comprises the steps of obtaining a single undifferentiated HES cell; mixing the single undifferentiated cell with an extracellular matrix (ECM) to encompass the cell; and inoculating the mixture onto feeder cells with a nutrient medium in a growth environment.

Once surviving, the single cell can proliferate. Further, a clonal embryonic stem cell line is established.

The method of obtaining a single undifferentiated HES cell is well known in the art. (see for example Amit et al., Dev. Biol. 227:271-278, 2000) Such method typically comprises the steps of selecting a group of cells from a cell culture and dissociating the group of cells into single cells. The preferred dissociation method of present invention is enzymatic degradation, especially using collagenase.

As used herein, the term "extracellular matrix (ECM)" refers to one or more substances that provide the conditions for supporting cell attachment and growth.

Particularly suitable for use with the present invention are Matrigel™, human extracellular matrix or other extracellular matrix components.

Matrigel™ is a solution of basement membrane prepared from Engelbreth-Holm-Swarm tumor cells, which transforms into gel at room temperature to form a reconstituted basement membrane before use.

Methods of preparing a human extracellular matrix are well known in the art (see, for example, U.S. Pat. No. 5,993, 844). Such methods typically include contacting the cells with 0.01-0.05 N NaOH or 0.1% Triton-X, the cells are rinsed in a rinsing agent and an extracellular matrix is yielded. Preferred human extracellular matrix of the present invention is an extracellular matrix derived from HES cells.

Suitable extracellular matrix components for the present invention include collagen, elastin, fibronectin, laminin, fibrillin and the like, alone or in various combinations. Preferred matrix of the present invention is collagen.

As used herein, the term "feeder cell" refers to cells of one type that are co-cultured with cells of another type, to provide an environment in which the cells of the second type can grow.

Methods of preparing feeder cells are well known in the art (see, for example, U.S. patent Pub. No. 20030143736; A.U. Pat. No. 729,377). Generally, the feeder cells may be fibroblasts or other types of cells, and the cells are inactivated by large-dose radiation before use, such as γ-ray, or by drugs, such as mitomycin C. After the inactivation process, the surviving cells lost the capability to proliferate, but retained their physiological functions, such as metabolism and synthesis of growth factors.

Commonly used feeder cells are primary mouse embryonic fibroblast (PMEF), a mouse embryonic fibroblast (MEF), a murine fetal fibroblast (MFF), human embryonic fibroblasts (HEF) human fetal muscle cells (HFM), human fetal skin cells (HFS), human adult skin cells, human foreskin fibroblasts (HFF), human adult fallopian tube epithelial cells (HAFT) or human marrow stromal cells (HMS). Preferred feeder cells of the present invention are HFF and MEF.

As used herein, the term "nutrient medium" refers to a culturing medium containing nutrients that promote the cells to proliferate. The nutrient medium may contain any of the following in an appropriate combination: isotonic saline, buffer, amino acids, serum or serum replacement, and other exogenously added factors.

Methods of preparing nutrient medium for culturing HES cells are well known in the art (see, for example, Reubinoff Be. et. al., Nat. Biotechnol. 18:399-404, 2002; Richards, M. et al., Nat. Biotechnol. 20:933-936, 2002).

A HES medium may typically contain 80% Dulbecco's Modified Eagles Medium (DMEM), 20% defined Fetal Calf Serum, 1% L-Glutamine, 0.5% penicillin/streptomycin, 1% non-essential amino acids, 1% Insulin-Transferrin-Selenium G supplement and 1 mM β-mercaptoethanol.

As used herein, the term "growth environment" refers to an environment in which cells of interest will proliferate in vitro. Temperatures of 37° C. and 5% $CO_2$ in air are generally adopted.

As used herein, the term "a group of cells" refers to one or more clusters of cells that have not been dissociated into single cells.

As used herein, the term "cell culture" refers to a composition comprising isolated cells of the same or a different type.

As is illustrated in the example sections which follows, single undifferentiated cells cultured under such conditions had a high survival rate and growth. In addition, these single cells had undifferentiated proliferation capacity and impact colony formation. Thus, the method of the present invention is useful for culturing single undifferentiated HES cells.

According to the present invention, there is yet provided a method of promoting the efficiency of gene transfer by using single cells. Methods for transfection and expression of genes in single cells of the present invention are standard to those in the art (see, for example, International Patent Publication No. WO 03/020920). Applicants have found that these single cells are useful in cell transfection, as they transfect at much higher frequencies than traditional cell colonies. Once the single cells are transfected successfully, the genetically altered cells can be expanded by the method of the present invention and be further used for gene expression studies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Example 1

Growth of Single Undifferentiated HES Cells Encompassed with ECM on Feeder Cells a) Single Undifferentiated HES Cells Preparation The undifferentiated HES cell line identified as HES-3 was used in this example. The undifferentiated HES cells were dissociated into a single-cell suspension by incubating in 200 u/ml collagenase type IV (Gibco) for about 5 minutes at 37° C. The single-cell suspension was centrifuged at 2,000 rpm for 5 minutes, and the supernatant was decanted. The pellet containing single cells was resuspended in an HES medium to form a single-cell suspension.

b) Extracellular Matrix Preparation (i) HES extracellular matrix was extracted from HES cells. The HES cells were removed by extraction with 1 ml 1% Triton X-100 (Sigma) for 30 minutes or 1 ml 0.05 N NaOH (Sigma) for 5 minutes. After removal of the lysed cells, the matrix was incubated in 100 µl HES medium.

(ii) Matrigel™ derives from the Engelbreth-Holmswarm mouse tumor cells. Matrigel™ was prepared before use in HES medium at a 1:20 dilution after unfrozen at 4° C.

(iii) Collagen III was prepared as following. 1 g Collagen III was dissolved in 100 ml 0.02N acetic acid (Merck) and diluted 1:10 in HES culture medium.

c) Feeder Cells Preparation

Mouse embryonic fibroblasts (MEF) or human foreskin fibroblasts (HFF) (from Animal Technology Research Institute, Taiwan) were used in this example. The feeder cells were grown to confluence in the presence of a feeder cell growth medium prepared from 90% Dulbecco's Modified Eagle Medium (DMEM) (Gibco), 10% fetal bovine serum (HyClone), 1% glutamine (Gibco) and 0.5% penicillin/streptomycin (Life Technologies). When the cells reached confluence, 10 µg/ml Mitomycin C (Sigma) was added to inactivate the fibroblasts.

After thoroughly washing the inactivated cells two times with PBS ($Ca^{2+}/Mg^{2+}$ free), the feeder cells were detached from the plastic by trypsinization with 0.25% trypsin-EDTA (Gibco). Once detached, the cells were centrifuged, the supernatant was decanted and the cell pellets were then seeded into culture dishes pre-coated with 0.1% gelatin (Sigma, 1% solution from Bovine Skin, diluted with sterile $H_2O$ prior to use) in the presence of the feeder cell growth medium. The feeder cells were cultured at 37° C. and 5% $CO_2$.

d) HES Medium

The culture medium used for undifferentiated HES cells consists of 80% Dulbecco's Modified Eagles Medium (DMEM, Gibco), which contains 20% FBS (Hyclone), 1 mM β-mercaptoethanol (Gibco), 1% non-essential amino acids (Gibco), 1% L-Glutamine (Gibco), and 1% Insulin-Transferrin-Selenium G supplement (Gibco).

e) Growth of Single Undifferentiated HES Cells Encompassed with Various ECM on MEF and HFF (i) Experimental group: 100 µl single cell suspension was mixed with 100 µl HES extracellular matrix, Matrigel or Collagen III respectively, and the mixtures were transferred to culture dishes with mitomycin-C treated MEF and HFF feeder cells in the presence of the HES medium. The medium was refreshed daily.

(ii) Control group: 100 µl of single cell suspension was directly placed onto mitomycin-C treated MEF and HFF feeder cells in the presence of the HES medium. The medium was refreshed daily.

Both experimental and control dishes were housed in the same incubators and monitored daily for 6 days for colony formation and growth (differentiated or undifferentiated).

f) Confirmation of Undifferentiation

The HES is characterized by tests well known in the art to ensure its pluripotency. For the purpose, the expression of alkaline phosphatase in the cells is estimated in this example.

Alkaline phosphatase expression was visualized using the Vector Red alkaline phosphatase substrate kit (Vector Lab). The kit was performed following the manufacturer's specifications. Briefly, growth medium was aspirated from the culture plate, then the cells were washed once in DPBS, and the working solution of substrate was applied. The cells were incubated with the substrate solution for a period of 15-20 minutes in the dark. The cells were then analyzed for alkaline phosphatase staining with phase-contrast light microscopy.

g) Experiment Results

Table 1 shows the number of colonies formed from single undifferentiated HES cells encompassed with various ECM on feeder cells. Preliminary data indicate that the undifferentiated HES cells encompassed with HES ECM had a high survival ratio. After 6 days culturing, these undifferentiated single cells encompassed with HES ECM showed good proliferation capacity and impact colony formation, but these undifferentiated single cells in the control group showed no colony formation. In comparison with cells encompassed with Matrigel™ or collagen III, the colonies derived from single undifferentiated ES cells with HES ECM spread out more rapidly.

Figure 2:
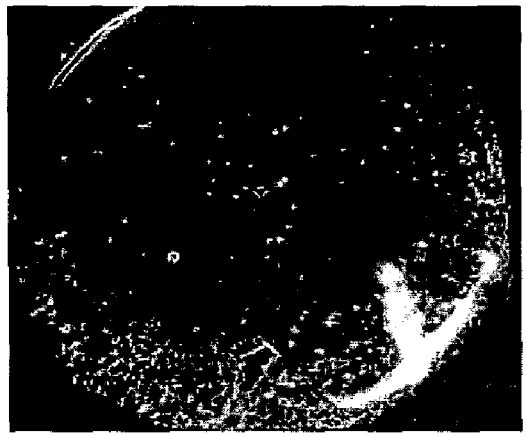
FIGS. 2a-d illustrate the expression of alkaline phosphatase of 6-day-old colonies derived from single undifferentiated HES-3 cells encompassed with various extracellular matrix on mitomycin-C treated mouse embryonic fibroblasts (MEF) feeder cells in the HES medium.
Figure 2:
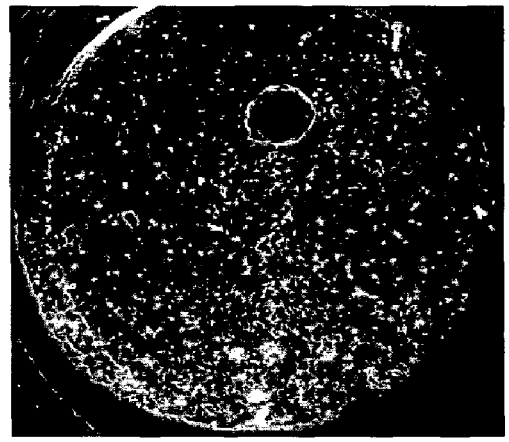
Figure 2:
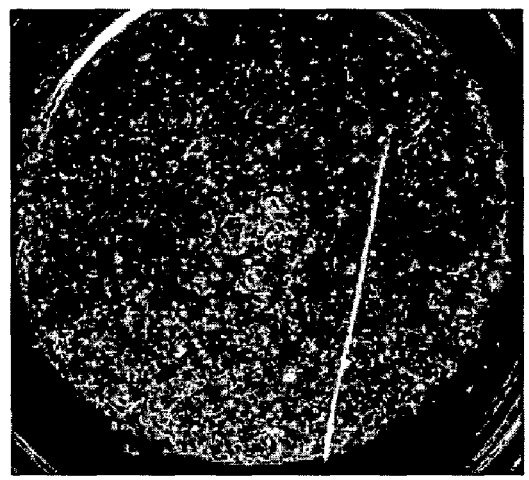
Figure 2:
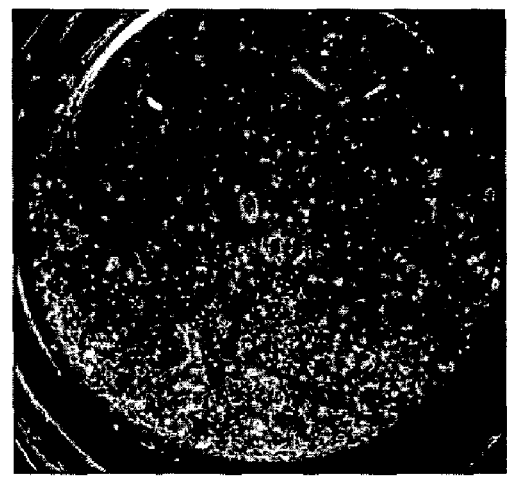

The pluripotency of a cell is characterized with undifferentiation status, and the ability of pluripotency can also be determined by alkaline phosphatase expression. FIG. 1 and FIG. 2 respectively illustrate the alkaline phosphatase expression of 6-day-old colonies derived from single undifferentiated HES-3 cells encompassed with various extracellular matrix (ECM) on mitomycin-C treated mouse embryonic fibroblasts (MEF) and human foreskin fibroblasts (HFF) in the HES medium. According to the FIGS. 1 and 2, a highly expressed alkaline phosphatase was observed in single undifferentiated cells encompassed with various extracellular matrix, and the results indicate the 6-day-old single clones have the ability of pluripotency.

Thus, the method of the present invention is useful for culturing single undifferentiated HES cells, that is, single HES cells can survive, form colonies and remain undifferentiated under such conditions. The method is also suitable for establishing single cell clones and creating new cell lines.

TABLE 1

The colony formation rate of single HES cells encompassed with various ECM on feeder cells.

| Feeder cells | Mean Number of HES cell colonies (±standard error) | | | |
| --- | --- | --- | --- | --- |
| | Control | HES ECM | Matrigel | Collagen III |
| MEF | 1.3 ± 2.3 | 13.0 ± 5.6 | 10.0 ± 3.5 | 12.0 ± 2.83 |
| HFF | 0.7 ± 1.2 | 10.5 ± 0.7 | 12.0 ± 5.7 | 3.0 ± 1.41 |

Example 2

HES Cell Transfection

To assess transfection efficiency of single cells, in comparison with cell colonies, HES cells were transfected with a plasmid encoding an enhanced green fluorescent protein (EGFP) under the transcriptional control of the phosphoglycerate kinase (PGK) promoter.

(i) Experimental group: Undifferentiated single cells suspended in 50 µl DMEM medium were prepared following the procedure described previously. 1.5 µl of transfection agent (FuGENE 6, Roche) was dissolved in another 50 µl DMEM medium. 0.5 µg of plasmid (EGFP encoded by PGK promoter) was mixed with the single cells suspension and transfection agent solution. The transfection reaction was kept at 37° C. for 1 hour. The transfected single cells were encompassed with HES extracellular matrix before being inoculated onto the Mitomycin C inactivated human foreskin fibroblast feeder cells in the HES medium. The medium was refreshed daily.

(ii) Control group: Undifferentiated HES cell colonies on mitomycin C inactivated human foreskin fibroblast feeders were transfected. 0.5 µg of plasmid (EGFP encoded by PGK promoter) was mixed with transfection agent solution and the mixture was applied to the undifferentiated cell colonies for 1 hour at 37° C. The medium was refreshed daily.

Both experimental and control dishes were housed in the same incubators and monitored daily for colony formation and growth. Several replicates were attempted.

After 2 days, the expression of EGFP was observed to estimate the transfection efficiency by fluorescence microscopy.

Figure 3:
FIGS. 3a-b illustrate the expression of enhanced green fluorescent protein (EGFP) of one colony derived from transfected single undifferentiated HES-3 cells encompassed with HES extracellular matrix on mitomycin-C treated human foreskin fibroblast (HFF) feeder cells in the HES medium.
Figure 3:
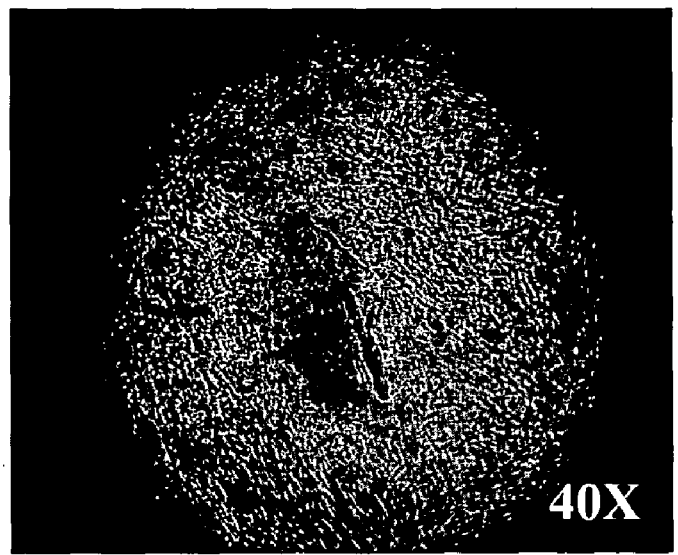
Figure 4:
FIGS. 4a-b illustrate the expression of enhanced green fluorescent protein (EGFP) of one transfected HES colony on mitomycin-C treated human foreskin fibroblast (HFF) feeder cells in the HES medium.
Figure 4:
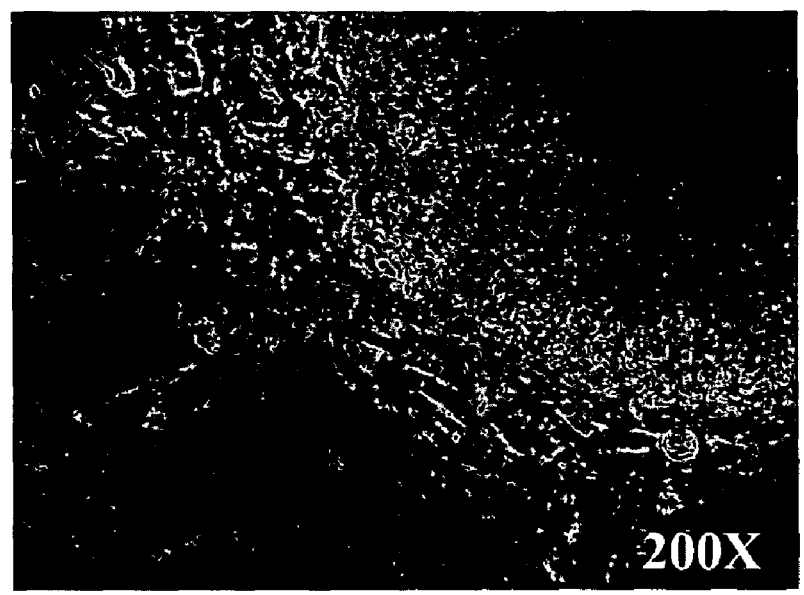

FIGS. 3 and 4 show the expression of EGFP. FIG. 3a is a fluorescence image of one colony derived from transfected single cells. FIG. 3b is a bright-field image of the same colony shown in FIG. 3a. FIG. 4a is a fluorescence image of one transfected cell colony. FIG. 4b is a computer-generated overlay of a bright-field and fluorescence image of the same colony shown in FIG. 4a. In comparison with cell colonies, the single cells have higher transfection efficiency. Such single cell clones can be further expanded into a gene modified ES cell line under a suitable growth environment. The gene modified ES cell line is useful for gene expression studies.

What is claimed is:

1. A method of culturing single undifferentiated human embryonic stem cells (HES), comprising:
    (a) obtaining single-and-undifferentiated HES cells;
    (b) mixing the cells with an extracellular matrix to form a mixture prior to step (c), wherein the extracellular matrix in the mixture encompasses the cells; and
    (c) inoculating the mixture onto the feeder cells with a nutrient medium.

2. The method of claim 1, wherein the human embryonic stem cells are HES-3.

3. The method of claim 1, wherein the extracellular matrix is a human extracellular matrix extracted from human embryonic stem cells.

4. The method of claim 1, wherein the extracellular matrix is prepared from basement membrane preparation extracted from Engelbreth-Holm-Swarm mouse sarcoma.

5. The method of claim 1, wherein the extracellular matrix is prepared from an isolated matrix component or the combination selected from the group consisting of collagen, elastin, fibronectin, laminin and fibrillin.

6. The method of claim 1, wherein the extracellular matrix is prepared from collagen.

7. The method of claim 1, wherein the feeder cells are selected from the group consisting of primary mouse embryonic fibroblasts (PMEF), mouse embryonic fibroblasts (MEF), murine fetal fibroblasts (MFF), human embryonic fibroblasts (HEF), human fetal muscle cells (HFM), human fetal skin cells (HFS), human adult skin cells, human foreskin fibroblasts (HFF), human adult fallopian tube epithelial cells (HAFT) and human marrow stromal cells (HMS).

8. The method of claim 1, wherein the feeder cells are mouse embryonic fibroblasts (MEF), human adult skin cells or human foreskin fibroblasts (HFF).

9. The method of claim 1, wherein the method of obtaining a single undifferentiated HES cells comprises:
    (a) selecting a group of undifferentiated cells from a cell culture; and
    (b) dissociating the group of undifferentiated cells into single cells.

10. The method of claim 9, wherein the dissociation method is enzymatic degradation.

11. The method of claim 10, wherein the enzymatic degradation is using collagenase.

12. The method of claim 1, wherein the method is used for establishing a clonal HES cell line.

13. The method of claim 1, wherein the method is suitable for gene transfection.

* * * * *